United States Patent [19]

Welch, Jr. et al.

[11] Patent Number: 4,536,518

[45] Date of Patent: Aug. 20, 1985

[54] ANTIDEPRESSANT DERIVATIVES OF CIS-4-PHENYL-1,2,3,4-TETRAHYDRO-1-NAPHTHALENAMINE

[75] Inventors: Willard M. Welch, Jr., Mystic; Charles A. Harbert, Waterford; B. Kenneth Koe, Gales Ferry; Allen R. Kraska, East Lyme, all of Conn.

[73] Assignee: Pfizer Inc., New York, N.Y.

[21] Appl. No.: 90,240

[22] Filed: Nov. 1, 1979

[51] Int. Cl.³ .................... A01N 33/02; C07C 87/64
[52] U.S. Cl. ................... 514/647; 514/555; 564/308
[58] Field of Search .......... 564/308; 424/316, 330; 268/501.1

[56] References Cited

U.S. PATENT DOCUMENTS 2,887,509  5/1959  Nash ............................ 424/316 X
3,704,323  11/1972  Krapcho ....................... 260/576
4,029,731  6/1977  Sarges .......................... 260/576 X

OTHER PUBLICATIONS

Burger, "Medicinal Chemistry", 3rd ed., Part II, pp. 1470, 1473–1475, 1478–1479, 1489, and 1490–1493, (1970).

Koe, B. K., "Molecular Geometry of Inhibitors of the Uptake of Catecholamines and Serotonin in Synaptosomal Preparations of Rat Brain", *Jour. Pharmac. and Exper. Ther.*, 199(3), pp. 649 to 661, (1976).

*Primary Examiner*—Robert V. Hines
*Attorney, Agent, or Firm*—Charles J. Knuth; Peter C. Richardson; Lawrence C. Akers

[57] ABSTRACT

Novel cis-isomeric derivatives of 4-phenyl-1,2,3,4-tetrahydro-1-naphthalenamine are useful as antidepressant agents. These novel compounds act to block the synaptosomal uptake of serotonin (5-hydroxy-tryptamine), thereby alleviating serotonin abnormalities at central receptor sites. The preferred embodiment is the enantiomer cis-(1S)-N-methyl-4-(3,4-dichlorophenyl)-1,2,3,4-tetrahydro-1-naphthalenamine and its pharmaceutically acceptable acid addition salts.

22 Claims, No Drawings

ANTIDEPRESSANT DERIVATIVES OF CIS-4-PHENYL-1,2,3,4-TETRAHYDRO-1-NAPHTHALENAMINE

BACKGROUND OF THE INVENTION

Drugs useful in the treatment of mental depression and apathy have generally fallen within at least one of three categories: (1) blockers of synaptosomal uptake of norepinephrine; (2) monoamine oxidase inhibitors; and (3) psychomotor stimulants. Serotonin, like norepinephrine, is known to be an important chemical messenger participating in the transmission of nerve impulses in the brain. These messengers are liberated at specific sites on pre-synaptic cells and received, to complete transmission of the impulse, at specific sites on post-synaptic cells. Their effect is then terminated by metabolism or by uptake into the pre-synaptic cells. Recently, the antidepressant activity of two new drugs, zimelidine and fluvoxamine, has been attributed to their ability to selectively block the uptake of serotonin (compared to norepinephrine blockade). It is thus becoming a widely held view in the medicinal chemistry field that drugs capable of blocking the pre-synaptosomal uptake of serotonin in the brain, thereby alleviating serotonin abnormalities at adjacent post-synaptic receptor sites, will comprise an additional major category of antidepressant agents.

U.S. Pat. Nos. 4,029,731 and 4,045,488 disclose a series of 4-phenyl-1,2,3,4-tetrahydro-naphthalen-1-amines and substituted amines useful as antidepressant agents. The trans-isomeric forms of these prior art compounds possess much greater antidepressant activity than the corresponding cis-isomeric forms. The preferred embodiment, the enantiomer trans-(1R)-N-methyl-4-phenyl-1,2,3,4-tetrahydro-1-naphthalenamine and its pharmaceutically acceptable acid addition salts, exhibits excellent synaptosomal norepinephrine uptake blocking activity.

SUMMARY OF THE INVENTION

We have now surprisingly discovered that certain novel cis-isomeric derivatives of 4-phenyl-1,2,3,4-tetrahydro-1-naphthalenamine are useful as antidepressant agents. The series of novel compounds of this invention consists of cis-isomeric bases of the formula

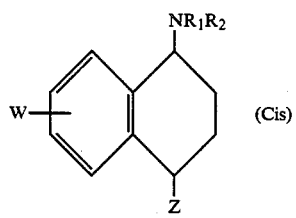

and the pharmaceutically acceptable acid addition salts thereof, wherein $R_1$ is selected from the group consisting of hydrogen and normal alkyl of from 1 to 3 carbon atoms, $R_2$ is normal alkyl of from 1 to 3 carbon atoms,

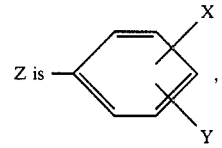

X and Y are each selected from the group consisting of hydrogen, fluoro, chloro, bromo, trifluoromethyl, alkoxy of from 1 to 3 carbon atoms and cyano, with at least one of X and Y being other than hydrogen, and W is selected from the group consisting of hydrogen, fluoro, chloro, bromo, trifluoromethyl and alkoxy of from 1 to 3 carbon atoms. The term "cis-isomeric" refers to the relative orientation of the $NR_1R_2$ and Z moieties on the cyclohexene ring (i.e. they are both oriented on the same side of the ring). Because both the 1- and 4- carbons of formula I are asymmetrically substituted, each cis- compound has two optically active enantiomeric forms denoted (with reference to the 1-carbon) as the cis-(1R) and cis-(1S) enantiomers. The preferred embodiment is the enantiomer cis-(1S)-N-methyl-4-(3,4-dichlorophenyl)-1,2,3,4-tetrahydro-1-naphthalenamine and its pharmaceutically acceptable acid addition salts.

The invention disclosed herein comprises the novel antidepressant compounds of formula I, the novel pharmaceutical compositions containing an amount effective in combatting mental depression of a compound of formula I as the essential active ingredient in a pharmaceutically acceptable carrier, and the novel method for combatting mental depression in a mentally-depressed subject which comprises administering to said subject an effective amount of a compound of formula I.

DETAILED DESCRIPTION OF THE INVENTION

The compounds of this invention exhibit antidepressant and anorectic activity in vivo in mammals, including human beings. At least a substantial portion of this activity results from their ability to block the synaptosomal uptake of serotonin (5hydroxytryptamine). The compounds of the invention possess negligible monoamine oxidase inhibition, anticholinergic and psychomotor stimulation activities. Effects upon the cardiovascular system are minimal.

By "pharmaceutically acceptable" acid addition salts is meant those salts which are non-toxic at the dosages administered. The pharmaceutically acceptable acid addition salts of the free bases of the invention are prepared by simply treating the free bases with various mineral and organic acids which form non-toxic acid addition salts, such as the hydrochloride, hydrobromide, hydroiodide, sulfate, bisulfate, phosphate, acid phosphate, acetate, lactate, maleate, fumarate, citrate, acid citrate, tartrate, bitartrate, succinate, gluconate and saccharate salts.

The preponderance of pharmaceutical activity of the cis-isomer compounds of formula I resides in the (1S)-enantiomeric forms thereof. Thus, one preferred group of the compounds of formula I consists of the (1S)-enantiomers and the racemic mixtures of (1S)- and (1R)-enantiomers of said compounds. This preferred group is referred to hereinafter as Group A.

One preferred group of the compounds of Group A consists of those wherein $R_1$ is hydrogen or methyl, $R_2$ is methyl and Z is selected from the group consisting of 3-chlorophenyl, 4-chlorophenyl, 3-trifluoromethylphenyl, 4-trifluoromethyl-phenyl, 3,4-dichlorophenyl, 3-bromophenyl, 4-bromophenyl, 4-methoxyphenyl and 3-trifluoromethyl-4-chloro-phenyl. These compounds exhibit synaptosomal uptake blocking activity that is highly selective for serotonin over norepinephrine. This is an important pharmacological property because, e.g., it is believed that the selective blockade of synaptosomal uptake of serotonin is beneficial in the treatment of certain types of mental depression.

Another preferred group of the compounds of Group A consists of those wherein $R_1$ is hydrogen or methyl, $R_2$ is methyl, W is hydrogen and Z is selected from the group consisting of 3,4-dichlorophenyl, 3-trifluoromethyl-phenyl, 4-chlorophenyl, 4-bromophenyl and 3-trifluoromethyl-4-chloro-phenyl. These compounds possess the highly desirable combination of excellent serotonin uptake blocking activity with excellent selectivity.

Particularly valuable are the following compounds, in either the (1S)-enantiomeric or (1S)(1R) racemic forms, and their pharmaceutically acceptable acid addition salts:

Cis-N-methyl-4-(3,4-dichlorophenyl)-1,2,3,4-tetrahydro-1-naphthalenamine;
Cis-N-methyl-4-(4-bromophenyl)-1,2,3,4-tetrahydro-1-naphthalenamine;
Cis-N-methyl-4-(4-chlorophenyl)-1,2,3,4-tetrahydro-1-naphthalenamine;
Cis-N-methyl-4-(3-trifluoromethyl-phenyl)-1,2,3,4-tetrahydro-1-naphthalenamine;
Cis-N-methyl-4-(3-trifluoromethyl-4-chlorophenyl)-1,2,3,4-tetrahydro-1-naphthalenamine;
Cis-N,N-dimethyl-4-(4-chlorophenyl)-1,2,3,4-tetrahydro-1-naphthalenamine;
Cis-N,N-dimethyl-4-(3-trifluoromethyl-phenyl)-1,2,3,4-tetrahydro-1-naphthalenamine; and
Cis-N-methyl-4-(4-chlorophenyl)-7-chloro-1,2,3,4-tetrahydro-1-naphthalenamine.

Of interest also is the (1R)-enantiomer of cis-N-methyl-4-(3,4-dichlorophenyl)-1,2,3,4-tetrahydro-1-naphthalenamine, which exhibits surprisingly good norepinephrine and serotonin uptake blocking activity.

The compounds of the invention may be prepared by methods familiar to those skilled in the art. Those compounds wherein $R_1$ is hydrogen and neither X nor Y is alkoxy may be prepared from the appropriate substituted benzophenone starting material via the following reaction scheme:

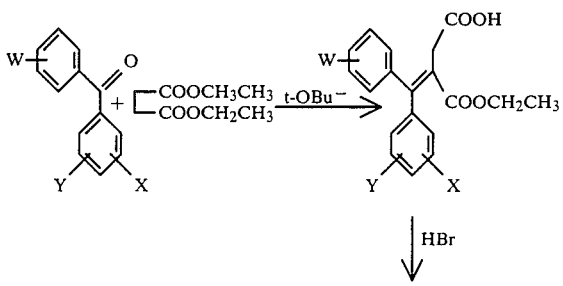

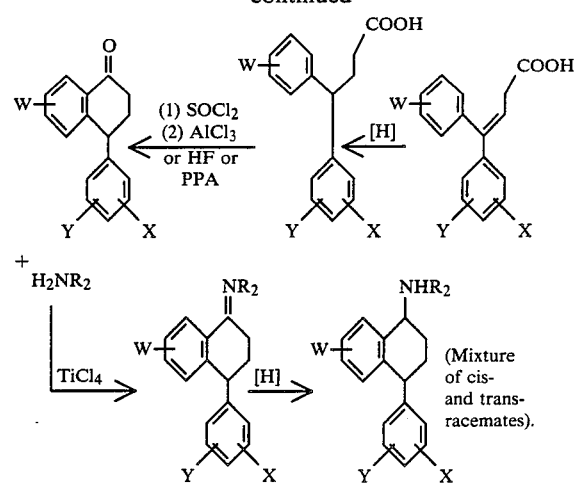

The first step in the above synthesis is a base-catalyzed Stobbe condensation of the substituted benzophenone with diethyl succinate. The next step is a hydrolysis and decarboxylation, e.g. with HBr. The resulting 4,4-diarylbut-3-enoic acid is reduced, e.g. with hydrogen over a catalyst or with HI and red phosphorus, to yield a 4,4-diarylbutanoic acid. The next step is a cyclization to yield a substituted tetralone, in the presence of, e.g., HF, polyphosphoric acid or thionyl chloride followed by $AlCl_3$. The substituted tetralone is condensed with the appropriate primary amine $H_2NR_2$ in the presence of an acid catalyst, e.g. $TiCl_4$, to yield a 1-imine, which is then reduced to the 1-alkylamine (mixture of cis- and trans-racemates), e.g. by catalytic hydrogenation or with a metal hydride complex.

Those compounds wherein $R_1$ is alkyl and neither X nor Y is alkoxy may also be prepared by the reaction scheme outlined above. The condensation of the substituted tetralone with the appropriate secondary amine $NHR_1R_2$ in the presence of an acid catalyst, e.g. $TiCl_4$, yields a 3,4-dihydro-1-dialkylamine compound, which is then reduced to the 1,2,3,4-tetrahydro-1-dialkylamine (mixture of cis- and trans-racemates), e.g. with sodium borohydride in the presence of acetic acid.

Certain of the substituted benzophenone starting materials are commercially available, including 4-chlorobenzophenone, 4,4'-dichloro-benzophenone, 4-fluorobenzophenone and 4-bromobenzophenone. Those not commercially available may be prepared by various well known methods, such as the reaction of a substituted benzoyl chloride with benzene in the presence of $AlCl_3$, or the reaction of (optionally substituted)phenyl magnesium bromide with a substituted benzonitrile.

Those compounds wherein $R_1$ is hydrogen, including those wherein either X or Y (or both) is alkoxy, may also be prepared from 1-tetralone or a substituted derivative thereof via the following reaction scheme:

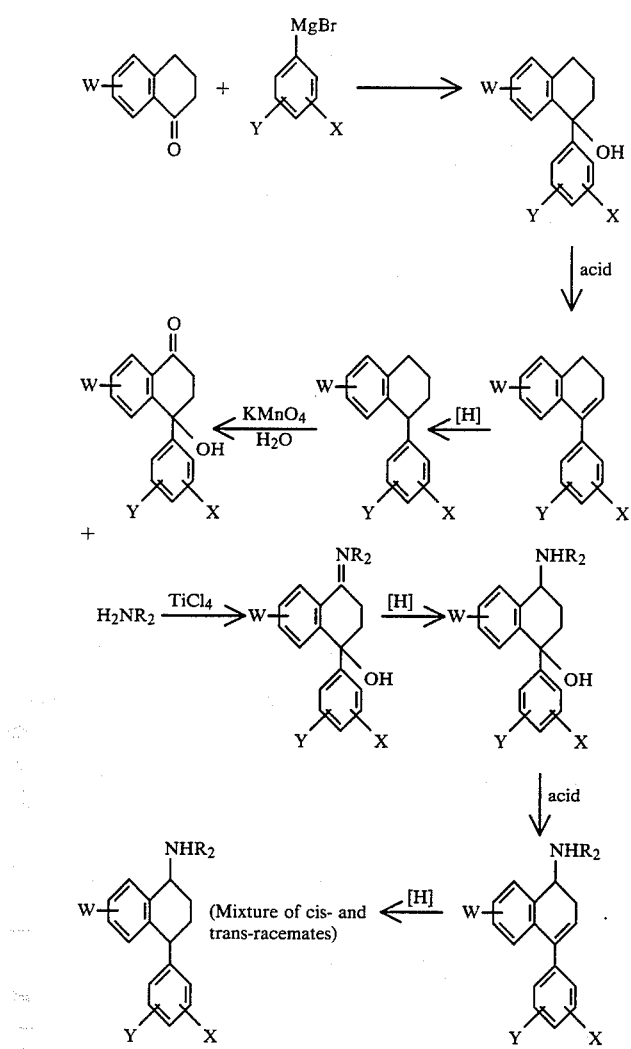

The first step in the above synthesis is a reaction of the tetralone with an appropriate Grignard reagent, followed by hydrolysis. The resulting compound is dehydrated with acid, followed by hydrogenation to yield a 1-(substituted phenyl)-tetralin compound (optionally substituted by W). This compound is oxidized by potassium permanganate in the presence of water to yield a 4-hydroxy-1-tetralone derivative. This substituted tetralone is condensed with the appropriate primary amine $H_2NR_2$ in the presence of an acid catalyst, e.g. $TiCl_4$, to yield a 1-imine, which is then reduced to a 1-alkylamine, e.g. with a metal hydride complex. The resulting 4-hydroxy-1-alkylamine is dehydrated with acid, and the dehydration product hydrogenated to yield the 1,2,3,4-tetrahydro-1-alkylamine compound (mixture of cis- and trans-racemates). In certain cases the second (dehydration) and third (hydrogenation) steps of the above synthesis can be omitted.

Those compounds wherein $R_1$ is alkyl may also be prepared by the reaction scheme outlined immediately above. The condensation of the 4-hydroxy-1-tetralone derivative with the appropriate secondary amine $HNR_1R_2$ in the presence of an acid catalyst, e.g. $TiCl_4$, yields a 3,4-dihydro-4-aryl-4-hydroxy-1-dialkylnaphthalenamine compound, which is then reduced to the 1,2,3,4-tetrahydro-4-aryl-4-hydroxy-1-dialkylnaphthalenamine, e.g. with sodium borohydride in the presence of acetic acid. The rest of the synthetic route is unchanged.

Certain of the optionally substituted tetralone starting materials are commercially available, including 1-tetralone. Those not commercially available may be prepared by synthesis methods well known to those skilled in the art.

The products of the synthetic methods described above are mixtures of cis- and trans-isomers. These isomers may be separated by methods known to those skilled in the art, e.g. fractional crystallization or chromatography. Trans-isomeric compounds are described in more detail in our concurrently filed patent application, entitled "Antidepressant Derivatives of Trans-4-phenyl-1,2,3,4-tetrahydro-1-naphthalenamine" U.S. Ser. No. 184,447, filed Sept. 5, 1985.

Resolution of the racemic cis-isomeric compounds of this invention into the (1S)- and (1R)-enantiomers is achieved by treating a solution of the cis-racemate free base with an optically active selective precipitant acid such as D-(−)-mandelic acid, L-(+)-mandelic acid, (+)-10-camphorsulfonic acid or (−)-10-camphorsulfonic acid, whereby the less soluble diastereomeric salt form is subsequently isolated as a crystalline precipitate.

Acid addition salts of the free bases of formula I (in either the racemic or optically active form) may be prepared by conventional procedures such as by mixing the amine base in a suitable solvent with the appropriate acid and recovering the salt by evaporation or by precipitation upon adding a non-solvent for the salt. Hydrochloride salts may readily be prepared by passing hydrogen chloride through a solution of the amine base in an organic solvent.

The activity of the compounds of the present invention as antidepressants and related pharmacological properties were determined by studying (1) their ability to affect the efforts of mice to escape from a swim-tank (Porsolt mouse "behavioral despair" test), (2) their ability to potentiate 5-hydroxytryptophan—induced behavioral symptoms in mice in vivo, (3) their ability to antagonize the serotonin-depleting activity of p-chloroamphetamine hydrochloride in rat brain in vivo, (4) their ability to block the uptake of serotonin, norepinephrine and dopamine by synaptosomal rat brain cells in vitro by the method of Koe, B., *Journal of Pharmacology and Experimental Therapeutics*, 199 (3), pp. 649–661 (1976), and (5) their ability to counteract reserpine hypothermia in mice in vivo (see U.S. Pat. No. 4,029,731).

As previously indicated, the cis-isomeric compounds of this invention are readily adapted to therapeutic use as antidepressant agents. The herein described cis-isomers of this invention can be administered as antidepressant agents by either the oral or parenteral routes of administration, without causing any significant untoward pharmacological side effects to occur in the subject to whom they are administered. In general, these antidepressant compounds are normally administered in dosages ranging from about 0.3 mg. to about 10 mg. per kg. of body weight per day, although variations will necessarily occur depending upon the conditions of the subject being treated and the particular route of administration chosen.

In connection with the use of the compounds of this invention for the treatment of depressed subjects, it is to be noted that these compounds may be administered either alone or in combination with pharmaceutically acceptable carriers by either of the routes previously indicated, and that such administration can be carried out in both single and multiple dosages. More particularly, the novel compounds of this invention can be administered in a wide variety of different dosage forms, i.e., they may be combined with various pharmaceutically-acceptable inert carriers in the form of tablets, capsules, lozenges, troches, hand candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of this invention are present in such dosage forms at concentration levels ranging from about 0.5% to about 90% by weight of the total composition, i.e., in amounts which are sufficient to provide the desired unit dosage. The compounds of this invention may exist in different polymorphic forms, i.e. different crystalline forms.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

For purposes of parenteral administration, solutions of compounds of the invention in sesame or peanut oil or in aqueous propylene glycol or N,N-dimethylformamide may be employed, as well as sterile aqueous solutions of the water-soluble, non-toxic mineral and organic acid addition salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

A typical dry solid pharmaceutical composition is prepared by blending the following materials together in the proportions by weight specified below:

Cis-(1S)-N-methyl-4-(3,4-dichlorophenyl)-1,2,3,4-tetrahydro-1-naphthalenamine hydrochloride: 50
  Sodium citrate: 25
  Alginic acid: 10
  Polyvinylpyrrolidone: 10
  Magnesium stearate: 5

After the dried composition is thoroughly blended, tablets are punched from the resulting mixture, each tablet being of such size that it contains 100 mg. of the active ingredient. Other tablets are also prepared in a similar fashion containing 5, 10, 25 and 50 mg. of the active ingredient, respectively, by using the appropriate amount of the naphthalenamine salt in each case.

Another typical dry solid pharmaceutical composition is prepared by combining the following materials together in the proportions by weight indicated below:
  Cis-(1S)-N-methyl-4-(3,4-dichlorophenyl)-1,2,3,4-tetrahydro-1-naphthalenamine hydrochloride: 50
  Calcium carbonate: 20
  Polyethylene glycol, average molecular weight, 4000: 30

The dried solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 50 mg. of the active ingredient.

The following examples illustrate the invention but are not to be construed as limiting the same.

EXAMPLE 1

Cis-(1S)(1R)-N-methyl-4-(3,4-dichlorophenyl)-1,2,3,4-tetrahydro-1-naphthalenamine Hydrochloride (A) 3,4-Dichlorobenzophenone Anhydrous AlCl$_3$ (219 g., 1.64 moles) was added in portions over a 35 to 40 min. period to a stirred solution of 3,4-dichlorobenzoyl chloride (313.5 g., 1.50 moles) in benzene (1.125 l.) and dichloromethane (75 ml.), with the mixture maintained at 3° to 5° C. during the addition period. The reaction mixture was held at 0° to 5° C. for another hour and then poured into 2.5 l. of ice/water and stirred until the complex had decomposed. The organic and aqueous layers were then separated and the organic layer combined with one ethyl acetate wash of the aqueous layer. The resulting organic solution was washed twice with water and once with saturated brine solution, dried (anhyd. MgSO$_4$), treated with decolorizing carbon and evaporated under vacuum to yield an off-white solid, which was recystallized from 400 ml. of hot ethyl acetate-pentane (156.8 g., 41% yield, m.p. 100°–102° C., elemental analysis calculated: 62.21% C; 3.21% H; 28.25% Cl; found: 62.17% C; 3.46% H; 28.06% Cl).

(B) 3-Ethoxycarbonyl-4-(3,4-dichlorophenyl)-4-phenyl-but-3-enoic Acid

A solution of 3,4-dichlorobenzophenone (398 g., 1.58 moles) in t-butyl alcohol (1500 ml.) was treated sequentially with potassium t-butoxide (169 g., 1.5 moles) and diethyl succinate (402 ml., 2.4 moles). A mildly exothermic reaction ensued and the initially clear solution set up as a solid mass. The reaction mixture was slowly heated to reflux, at which it became a stirrable white suspension, and then stirred at reflux under nitrogen for about 16 hours. The reaction mixture was then cooled and poured into 2 liters of ice/water. The resulting mixture was acidified with 10% HCl and extracted with ethyl acetate (3×1 l.). The combined ethyl acetate extract was extracted with 1N NH$_4$OH (3×1 l.) and the combined aqueous basic extract washed with ethyl acetate (2 l.), cooled to 0° to 5° C., acidified slowly to a pH below 1.0 with concentrated HCl and extracted with ethyl acetate (4×2 l.). The combined ethyl acetate extract was dried (MgSO$_4$) and evaporated under vacuum to a light yellow oil slightly contaminated with diethyl succinate (477 g., 80% yield). An analytical sample was crystallized from petroleum ether (m.p. 128°–130° C., elemental analysis calculated: 60.17% C; 4.26% H; 18.70% Cl; found: 60.37% C; 4.35% H; 18.61% Cl).

(C) 4-(3,4-Dichlorophenyl)-4-phenylbut-3-enoic Acid

A suspension of 3-ethoxycarbonyl-4-(3,4-dichlorophenyl)-4-phenylbut-3-enoic acid (227 g., 0.60 mole) in 48% aqueous HBr:glacial acetic acid (1:1, 1.80 l.) was stirred at reflux for 36 hours and then cooled to room temperature. A gum separated from the reaction mixture, which was isolated by decantation of the aqueous layer and then dissolved in ethyl acetate (2 l.). The resulting organic solution was extracted with 10% aqueous NH$_4$OH (2×2 l.). The combined extract was cooled to 0° to 5° C., acidified slowly to a pH below 1.0 with concentrated HCl and extracted with ethyl acetate (4×1 l.). The combined ethyl acetate extract was washed with water, dried (MgSO$_4$) and evaporated under vacuum to a light brown oil (120 g.), which was crystallized from hexane (91.4 g., 50% yield, m.p. 115°–120° C.). An analytical sample of the named compound was recrystallized from hot ethyl acetate-hexane (elemental analysis calculated: 62.58% C; 3.94% H; 23.10% Cl; found: 62.66% C; 4.02% H; 23.22% Cl).

(D) 4-(3,4-Dichlorophenyl)-4-phenylbutanoic Acid

A solution of 4-(3,4-dichlorophenyl)-4-phenylbut-3-enoic acid (223 g., 0.73 mole) in ethyl acetate (2 l.) was hydrogenated over 8 grams of 5% Pd/C catalyst at atmospheric pressure and room temperature until hydrogen uptake ceased (about 24 hours). The catalyst was separated by filtration and the filtrate evaporated under vacuum to a light brown oil containing traces of solvent (ca. 100% yield). An analytical sample of the named compound was crystallized from hexane (m.p. 118°–120° C., elemental analysis calculated: 62.17% C; 4.57% H; 22.94% Cl; found: 62.08% C; 4.56% H; 23.16% Cl).

(E) 4-(3,4-Dichlorophenyl)-3,4-dihydro-1-(2H)-naphthalenone

A solution of 4-(3,4-dichlorophenyl)-4-phenylbutanoic acid (228 g., 0.74 mole) in toluene (1.2 l.) was treated with thionyl chloride (66 ml., 0.90 mole) and the resulting solution heated at reflux for 75 minutes, with provision made for trapping HCl gas given off from the refluxing reaction solution. The reaction solution was then evaporated under vacuum to about 230 g. of a light brown oil. The oil was dissolved in carbon disulfide (360 ml.) and the resulting solution added to a well stirred suspension of AlCl$_3$ (1.5 kg., 12.5 moles) in carbon disulfide (1.20 l.), with the mixture held below 8° C. during the addition period, forming a brown mass. After the addition was completed, the reaction mixture was stirred for about 16 hours at room temperature and then slowly poured on ice (vigorous reaction). The resulting suspension was extracted with ethyl acetate (2×4 l.). The combined extract was washed with water, washed with saturated aqueous sodium bicarbonate solution, dried and evaporated under vacuum to a residue, which was crystallized from hexane (500 ml.) to yield the named product (104.1 g., 48% yield, m.p. 99°–101° C., elemental analysis calculated: 66.00% C; 4.16% H; found: 66.06% C; 4.23% H).

(F) Title Compound (Cis-Racemate)

A solution of 4-(3,4-dichlorophenyl)-3,4-dihydro-1-(2H)naphthalenone (50 g., 0.17 mole) in tetrahydrofuran (800 ml.) was cooled to 0° to 5° C. and treated with 52 ml. (1.20 moles) of methylamine (condensed at 0° C.). Titanium tetrachloride (10 ml. 0.087 mole) was added dropwise to the resulting solution (vigorous reaction), with the reaction mixture stirred at below 10° C. during the addition period. After the addition was completed, the reaction mixture was stirred for 17 hours at room temperature under nitrogen and then filtered. The solids were washed thoroughly with tetrahydrofuran and the combined filtrates were concentrated under vacuum to 600 ml. to remove excess methylamine. Further evaporation of an aliquot to dryness and trituration with hexane yielded the Schiff base (m.p. 145°–146° C.).

The Schiff base-containing concentrate was hydrogenated for 2 hours over 5.0 g. of 10% Pd/C catalyst at atmospheric pressure and room temperature. Hydrogen uptake ceased within the 2 hour reaction period. After removal of the catalyst by filtration, the reaction mixture was evaporated under vacuum to a residue. The residue was dissolved in anhydrous ether (1 liter) and the resulting solution treated with gaseous hydrogen chloride to yield a white precipitate.

The above precipitate was combined with the product from a second run starting with 0.15 mole 4-(3,4-dichlorophenyl)-3,4-dihydro-1-(2H)naphthalenone. The combined HCl salt, which contained about 70% cis-racemate and 30% trans-racemate of N-methyl-4-(3,4-dichlorophenyl)-1,2,3,4-tetrahydro-1-naphthalenamine hydrochloride, was dissolved in hot methanol (2 l.). Upon addition of ether (1200 ml.) and cooling overnight, the title compound precipitated (47 g., m.p. 290°–291° C.). The supernatant was evaporated under vacuum to dryness and the residue triturated with acetone. The triturated residue (ca. 90% cis-racemate, 10% trans-racemate) was recrystallized from methanol:ether (1:1) to yield another 20 g. of the title compound (m.p. 289°–290° C.). The total yield (67 g.) from the naphthalenone was 68% (elemental analysis calculated: 59.58% C; 5.29% H; 4.09% N; 31.04% Cl; found: 59.79% C; 5.40% H; 4.16% N; 30.83% Cl).

EXAMPLE 2

Cis-(1S)-N-methyl-4-(3,4-dichlorophenyl)-1,2,3,4-tetrahydro-1-naphthalenamine Hydrochloride 67.1 g. of cis-(1S)(1R)-N-methyl-4-(3,4-dichlorophenyl)-1,2,3,4-tetrahydro-1-naphthalenamine hydrochloride was partitioned between 20% aqueous NaOH and ethyl acetate to yield a solution of the cis-racemate free base (60.2 g., 0.197 mole) in ethyl acetate. This solution was dissolved in absolute ethanol (600 ml.) and the resulting solution treated with D-(−)-mandelic acid (29.94 g., 0.197 mole). The resulting mixture was warmed on a steam bath to effect solution and then held overnight at room temperature to afford a white crystalline solid. This solid was separated by filtration, washed with ether and air dried (38.7 g., m.p. 188°–189° C.), and then recrystallized from hot absolute ethanol (32.6 g., m.p. 190°–191° C.). An additional crop (4.4 g., m.p. 190°–191° C.) was obtained by evaporation of the mother liquors under vacuum to residues, followed by crystallization of the residues from boiling ethanol (150 ml.).

The combined crops of mandelate salt were suspended in ethyl acetate (about 2 l.). The ethyl acetate suspension was treated with 10% aqueous NaOH solution, therby converting the amine to the free base. The resulting ethyl acetate solution was then dried, diluted with ether (2 l.) and then treated with excess gaseous hydrogen chloride to give a gelatinous suspension which crystallized overnight. The crystalline HCl salt product was separated by filtration, washed with ether and air dried [25.96 g., 39% yield, m.p. 243°–245° C., $[\alpha]_D^{23} = +37.9°$ (CH$_3$OH, C=2), elemental analysis calculated: 59.58% C; 5.29% H; 4.09% N; 31.04% Cl; found: 59.42% C; 5.24% H; 4.05% N; 30.84% Cl].

EXAMPLE 3

Cis-(1R)-N-methyl-4-(3,4-dichlorophenyl)-1,2,3,4-tetrahydro-1-naphthalenamine Hydrochloride In like manner to that described in Example 2 the named compound was prepared by using L-(+)-mandelic acid in place of D-(−)-mandelic acid as the selective precipitant [m.p. 243°–245° C., $[\alpha]_D^{23} = -37.25°$ (methanol), elemental analysis calculated: 59.58% C; 5.29% H; 4.09% N; found: 58.43% C; 5.57% H; 3.91% N].

EXAMPLES 4–6

Cis-N-methyl-4-(4-chlorophenyl)-1,2,3,4-tetrahydro-1-naphthalenamine Hydrochloride In like manner to that described in Examples 1–3 the named compound was prepared from commercially available 4-chlorobenzophenone and resolved into its enantiomeric forms:

| Example Number | Enantiomer | M.P. (°C.) | $[\alpha]_D^{23}$ (methanol) | Molecular Formula | Calculated (%) C | H | N | Found (%) C | H | N |
|---|---|---|---|---|---|---|---|---|---|---|
| 4 | Racemate | 267–269 | 0 | C$_{17}$H$_{18}$NCl.HCl | 66.24 | 6.21 | 4.55 | 66.33 | 6.32 | 4.61 |
| 5 | 1S | 232–234 | +38.9° | C$_{17}$H$_{18}$NCl.HCl | — | — | — | — | — | — |
| 6 | 1R | 232–234 | −41.0° | C$_{17}$H$_{18}$NCl.HCl | — | — | — | — | — | — |

EXAMPLE 7

Cis-(1S)(1R)-N-methyl-4-(4-fluorophenyl)-1,2,3,4-tetrahydro-1-naphthalenamine Hydrochloride (A) 3-Ethoxycarbonyl-4-(4-fluorophenyl)-4-phenylbut-3-enoic Acid A solution of commercially available 4-fluorobenzophenone (42 g., 0.21 mole), diethyl succinate (43.6 g., 0.25 mole) and potassium t-butoxide (23.7 g., 0.21 mole) in t-butanol (250 ml.) was stirred at reflux for 6 hours and then stirred at room temperature for an additional 16 hours. The reaction mixture was then acidified with 6N hydrochloric acid (200 ml.), evaporated under vacuum to remove the t-butanol and extracted with ether (2×250 ml.). The combined ether extract was extracted with 10% aqueous ammonium hydroxide (2×350 ml.). The combined aqueous extract was washed with ether (2×200 ml.), re-acidified with 6N hydrochloric acid and extracted again with ether (2×400 ml.). The combined ether extract was dried (MgSO$_4$), filtered and evaporated under vacuum to an oil, which was crystalized by dissolution in hexane (100 ml.) followed by scratching the flask to initiate crystallization (48 g., 70% yield, m.p. 98°–99° C., elemental analysis calculated: 69.50% C; 5.22% H; 5.78% F; found: 69.34% C; 5.36% H; 6.09% F).

(B) 4-(4-Fluorophenyl)-4-phenylbut-3-enoic Acid

3-Ethoxycarbonyl-4-(4-fluorophenyl)-4-phenylbut-3-enoic acid (47 g., 0.143 mole) was added to a mixture of glacial acetic acid (1000 ml.) and 48% aqueous hydrobromic acid (500 ml.), and the resulting mixture stirred at reflux for 16 hours. The reaction mixture was then concentrated under vacuum and the concentrate extracted with ether (3×500 ml.). The combined ether extract was extracted with 4% aqueous ammonium hydroxide (5×200 ml.). The combined aqueous extract was acidified with 6N hydrochloric acid to a pH of 6.5 and extracted again with ether (3×250 ml.). The combined ether extract was dried (MgSO$_4$), filtered and evaporated under vacuum to an oil, which solidified on standing. Trituration with hexane gave 15 g. of the named product (47% yield, m.p. 98°–100° C., elemental analysis calculated: 74.99% C.; 5.11% H; 7.41% F; found: 74.69% C; 5.40% H; 7.17% F).

(C) 4-(4-Fluorophenyl)-4-phenylbutanoic Acid

A solution of 4-(4-fluorophenyl)-4-phenylbut-3-enoic acid (15 g., 0.068 mole) in ethanol (200 ml.) was hydrogenated over 1.0 g. of 10% Pd/C catalyst for 2 hours at room temperature and 50 psi H$_2$. The reaction mixture was then filtered and evaporated under vacuum to yield a solid, which was recrystallized from an ether/petroleum ether mixture (10.6 g., 70% yield, m.p. 75°–75.5° C., elemental analysis calculated: 74.40% C; 5.85% H; 7.36% F; found: 74.62% C; 5.87% H; 7.15% F).

(D) 4-(4-Fluorophenyl)-alpha-tetralone 4-(4-Fluorophenyl)-4-phenylbutanoic acid (5 g., 0.019 mole) was treated with anhydrous hydrofluoric acid (20 ml.) and the resulting mixture stirred for 16 hours at room temperature. The reaction mixture was then diluted with water (100 ml.) and extracted with ether (200 ml.). The ether extract was washed with saturated aqueous sodium bicarbonate solution (50 ml.), washed with water (50 ml.), dried (MgSO$_4$), filtered and evaporated under vacuum to yield a solid, which was recrystallized from boiling hexane (3.2 g., 69% yield, m.p. 74°–75° C., elemental analysis calculated: 79.98% C; 5.45% H; found: 80.00% C; 5.66% H).

(E) Title Compound (Cis-Racemate)

A solution of 4-(4-fluorophenyl)-alpha-tetralone (3.0 g., 0.012 mole) in toluene (50 ml.) was cooled to 10° C. and treated at that temperature with methylamine (2.0 g., 0.064 mole) and then titanium tetrachloride (dropwise addition, 1.73 g., 0.009 mole). The reaction mixture was then stirred for 16 hours at room temperature, filtered and evaporated under vacuum to yield a crude 1-imine solid. The crude imine was dissolved in methanol (50 ml.), the methanol solution treated with sodium borohydride (1.0 g., 0.026 mole) and the resulting mixture stirred for 16 hours at room temperature. The reaction mixture was then evaporated under vacuum to an oily solid, which was dissolved in ether (200 ml.). The ether solution was washed with water (3×50 ml.), dried (MgSO$_4$), filtered and evaporated under vacuum to an oil. The oil was chromatographed on silica gel, using an ethyl acetate/hexane/diethylamine (16/16/0.3) solvent mixture for elution, to separate the cis- and trans-isomers. The cis-isomer was eluted first and converted to its hydrochloride salt by treating the eluted fractions with gaseous hydrogen chloride. This hydrochloride salt was recrystallized from a mixture of methanol and ether to give 380 mg. of the title compound (cis-racemate, 11% yield, m.p. 281°–282° C., elemental analysis calculated: 69.98% C; 6.56% H; 4.80% N; found: 69.79% C; 6.48% H; 4.78% N).

EXAMPLES 8-14

In like manner to that described in Examples 2, 3 and 7, the following cis-isomeric compounds were prepared from the appropriate substituted benzophenones and, in certain instances, resolved into their enantiomeric forms:

5.06% H; 4.13% N). In place of step 7D. the following procedure was employed:
(D) 4-(4-Chlorophenyl)-7-chloro-alpha-tetralone
4,4-Di(4-chlorophenyl)butanoic acid (3.5 g., 0.0113 mole) was treated with polyphosphoric acid (80 g.) and the resulting mixture treated for 4 hours at 120° C. The reaction mixture was then poured onto crushed ice and the product extracted with ether (3×150 ml.). The combined ether extract was washed with saturated

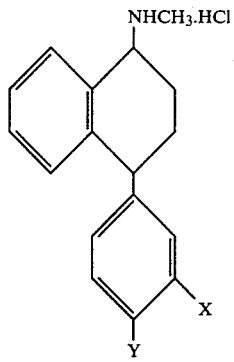

| Example # | X | Y | Enantiomer | M.P. (°C.) | $[\alpha]_D^{20}$ (ethanol) | Molecular Formula | Elemental Analysis Calculated (%) | | | | Found (%) | | | |
|---|---|---|---|---|---|---|---|---|---|---|---|---|---|---|
| | | | | | | | C | H | N | F | C | H | N | F |
| 8 | H | CF$_3$ | Racemate | 274-275 | 0 | C$_{18}$H$_{18}$NF$_3$.HCl | 63.24 | 5.60 | 4.10 | — | 62.98 | 5.58 | 4.08 | — |
| 9$^a$ | H | CF$_3$ | 1S | 208.5-210 | +32.8° | C$_{18}$H$_{18}$NF$_3$.HCl | — | — | — | — | — | — | — | — |
| 10$^a$ | H | CF$_3$ | 1R | 207-208.5 | −33.0° | C$_{18}$H$_{18}$NF$_3$.HCl | — | — | — | — | — | — | — | — |
| 11 | CF$_3$ | H | Racemate | 260-261 | 0 | C$_{18}$H$_{18}$NF$_3$.HCl | 63.24 | 5.60 | 4.10 | 16.67 | 63.08 | 5.59 | 4.11 | 16.79 |
| 12 | CF$_3$ | Cl | Racemate | 253-254 | 0 | C$_{18}$H$_{17}$NF$_3$Cl.HCl.½H$_2$O | 56.21 | 4.83 | 3.59 | — | 56.12 | 4.97 | 3.64 | — |
| 13 | CF$_3$ | Cl | 1S | 228-230 | +27.8° | C$_{18}$H$_{17}$NF$_3$Cl.HCl | — | — | — | — | — | — | — | — |
| 14 | CF$_3$ | Cl | 1R | 228-229.5 | −28.5° | C$_{18}$H$_{17}$NF$_3$Cl.HCl | — | — | — | — | — | — | — | — |

$^a$(+)-10-camphorsulfonic acid and (−)-10-camphorsulfonic acid were used in place of D-(−)-mandelic acid and L-(+)-mandelic acid to resolve racemate of Example 8 into enantiomers of Examples 9 and 10, respectively.

The appropriate substituted benzophenone starting materials for Examples 8-14 were prepared as shown below for 4-trifluoromethyl-benzophenone:
(A) 4-Trifluoromethyl-benzophenone
2.91M phenyl magnesium bromide (90 ml., 0.26 mole) was added dropwise over a 45 minute period to a solution of 4-trifluoromethyl-benzonitrile (40 g., 0.23 mole) in ether (400 ml.) and the resulting mixture stirred for 3 days at room temperature. The reaction mixture was then cooled in an ice-water bath, treated slowly with saturated aqueous ammonium chloride solution (150 ml.) and then treated with 1N HCl (100 ml.). The ether layer was removed and the aqueous layer extracted with ether (2×200 ml.). The three ether layers were combined, washed with 1N HCl (2×100 ml), washed with water (2×200 ml.), dried (MgSO$_4$), treated with activated carbon, filtered, and evaporated under vacuum to yield a solid, which was then crystallized from 200 ml. of hot hexane (36 g., 62% yield, m.p. 107°-108° C.). An analytical sample of the named compound was recrystallized from hexane (m.p. 116°-118° C.).

EXAMPLE 15

Cis-(1S)(1R)-N-methyl-4-(4-chlorophenyl)-7-chloro-1,2,3,4-tetrahydro-1-naphthalenamine Hydrochloride In like manner to that described in Example 7 A-C and E, the named compound (cis-racemate) was prepared from commercially available 4,4'-dichlorobenzophenone (m.p. 300°-301° C., elemental analysis calculated: 59.58% C; 5.29% H; 4.09% N; found: 59.64% C;

aqueous sodium bicarbonate solution (3×100 ml.), washed with water (100 ml.), dried (MgSO$_4$), filtered and evaporated under vacuum to yield the desired tetralone (2.2 g., 67% yield, m.p. 106°-107° C.).

EXAMPLE 16

Cis-(1S)(1R)-N-methyl-4-(4-bromophenyl)-1,2,3,4-tetrahydro-1-naphthalenamine Hydrochloride In like manner to that described in Example 7 A, B and E and Example 15 D, the named compound (cis-racemate) was prepared from commercially available 4-bromobenzophenone (m.p. 274°-275° C., elemental analysis calculated: 57.89% C; 5.43% H; 3.97% N; found: 57.48% C; 5.29% H; 3.95% N). In place of step 7C, the following procedure was employed:
(C) 4-(4-Bromophenyl)-4-phenylbutanoic Acid
A solution of 4-(4-bromophenyl)-4-phenylbut-3-enoic acid (5.0 g., 0.0157 mole) in glacial acetic acid (50 ml.) was treated with 56.9% aqueous hydriodic acid (22.5 ml.) and red phosphorus (4.5 g.) and the resulting mixture stirred at reflux for 16 hours. The reaction mixture was then cooled to room temperature, diluted with saturated aqueous sodium chloride solution (250 ml.) and extracted with methylene chloride (250 ml.). The extract was washed with saturated aqueous sodium chloride solution (2×100 ml.), dried (MgSO$_4$) and evaporated under vacuum to the desired butanoic acid derivative, which was used in the next step without further purification (5 g., oil, ca. 99% yield).

EXAMPLE 17

Cis-(1S)(1R)-N-methyl-4-(4-methoxyphenyl)-1,2,3,4-tetrahydro-1-naphthalenamine Hydrochloride (A) 1-Hydroxy-1-(4-methoxyphenyl)tetralin A solution of 4-bromo-anisole (25 g., 0.134 mole) in tetrahydrofuran (100 ml.) was prepared. Magnesium (3.24 g., 0.123 mole) was treated with a small portion of this solution and heated until a reaction started (55° C.). The remainder of the solution was added dropwise and, after the addition was complete, the mixture was stirred for 2 hours at 55° C. The reaction mixture was then cooled to room temperature and a solution of 1-tetralone (17.92 g., 0.123 mole) in tetrahydrofuran (100 ml.) slowly added. Stirring was continued at room temperature for 16 hours after the addition was complete. Ether (200 ml.) and water (200 ml.) were then added to the reaction mixture, followed by 10% aqueous ammonium chloride solution (100 ml.). The ether layer was separated, dried ($MgSO_4$), filtered and evaporated under vacuum to an oil, which was used without further purification in the next step (18 g., 58% yield).

(B) 1-(4-Methoxyphenyl)-3,4-dihydro-naphthalene

A solution of 1-hydroxy-1-(4-methoxyphenyl)tetralin (18 g., 0.071 mole) in toluene (250 ml.) was treated with para-toluenesulfonic acid (5 mg.) and the resulting solution stirred at reflux for 16 hours, with complete water removal accomplished by means of a Dean-Stark trap. The reaction mixture was then cooled to room temperature, washed sequentially with 10% aqueous sodium bicarbonate solution (100 ml.), water (100 ml.) and saturated aqueous sodium chloride solution (100 ml.), dried ($MgSO_4$) and evaporated under vacuum to an oil, which was purified by silica gel chromatography (elution with a hexane-toluene gradient) to give 12 g. of the named compound (67% yield, oil).

(C) 1-(4-Methoxyphenyl)tetralin 1-(4-Methoxyphenyl)-3,4-dihydro-naphthalene (12 g., 0.051 mole) was added to a mixture of 10% Pd on carbon catalyst (1.0 g.) and ethanol (250 ml.) and hydrogenated for 4 hours at room temperature and 50 psi of $H_2$. The reaction mixture was then filtered and evaporated under vacuum to an oil, which was used in the next step without further purification (11.2 g., 92.5% yield).

(D) 4-Hydroxy-4-(4-methoxyphenyl)-1-tetralone 1-(4-Methoxyphenyl)tetralin (11.2 g., 0.047 mole) was dissolved in a solution of potassium permanganate (36.7 g.) in acetone (1.6 l) and water (33 ml.), and the resulting solution stirred at reflux for 16 hours. The reaction mixture was then filtered, treated again with potassium permanganate (36.7 g.) and stirred at reflux for another 16 hours. This process was continued until a total of three reaction cycles had been run. After the third 16 hour reaction period, the reaction mixture was filtered, treated with activated charcoal, filtered and evaporated under vacuum to a residue. The residue was taken up in ethyl acetate (200 ml.) and the ethyl acetate solution washed with saturated aqueous sodium chloride solution (200 ml.), filtered, washed again with saturated aqueous sodium chloride solution (200 ml.), dried ($MgSO_4$), filtered and evaporated under vacuum to yield a solid, which was recrystallized from a mixture of ethyl acetate and hexane (3.9 g., 23% yield).

(E) N-methyl-4-hydroxy-4-(4-methoxyphenyl)-1,2,3,4-tetrahydro-1-naphthalenamine

A solution of 4-hydroxy-4-(4-methoxyphenyl-1-tetralone (3.9 g., 0.0138 mole) in tetrahydrofuran (40 ml.) was cooled to 0° C. and the cooled solution treated with methylamine (5 ml.) followed by dropwise addition of titanium tetrachloride (1 ml.). The resulting mixture was stirred for 16 hours at room temperature, filtered and evaporated under vacuum to an oil, which was dissolved in absolute ethanol (20 ml.). The ethanol solution was treated with sodium borohydride (1.0 g., 0.0264 mole) and stirred for 1 hour at room temperature. The reaction mixture was then evaporated under vacuum to a residue and the residue taken up in ethyl acetate (125 ml.). The ethyl acetate solution was washed with water (125 ml.), washed with saturated aqueous sodium chloride solution (125 ml.), dried ($MgSO_4$), filtered and evaporated under vacuum to an oil, which was used in the next step without further purification (3.4 g., 83% yield, mixture of cis- and trans-isomers).

(F) N-methyl-4-(4-methoxyphenyl)-1,2-dihydro-1-naphthalenamine Hydrochloride

A solution of N-methyl-4-hydroxy-4-(4-methoxyphenyl)-1,2,3,4-tetrahydro-1-naphthalenamine (1.9 g., 0.0069 mole, mixture of cis- and trans-isomers) in ether (50 ml.) was treated with gaseous hydrogen chloride. The solution was then evaporated under vacuum to yield a white solid, which was recrystallized from ethyl acetate (1.5 g., 72% yield, m.p. 221°-222° C.).

(G) Title Compound (Cis-Racemate)

N-methyl-4-(4-methoxyphenyl)-1,2-dihydro-1-naphthalenamine hydrochloride (1.5 g., 0.0049 mole) was mixed with ethanol (30 ml.) and 10% palladium on carbon catalyst (250 mg.) and hydrogenated for 4 hours at room temperature and 45 psi of $H_2$. The reaction mixture was then filtered and evaporated under vacuum to a residue. The residue was chromatographed on silica gel (elution with ethyl acetate containing 1% ammonium hydroxide) to separate the cis- and trans-isomers. The cis-isomer was converted to the hydrochloride salt, which was recrystallized from a mixture of chloroform and ether (221 mg., 15% yield, m.p. 224°-226° C., elemental analysis calculated: 71.15% C; 7.29% H; 4.61% N; found: 70.61% C; 7.52% H; 4.64% N).

EXAMPLES 18-19

In like manner to that described in Example 17 the following compounds (cis-racemates) were prepared from 2-bromo-anisole and 3-bromo-anisole:

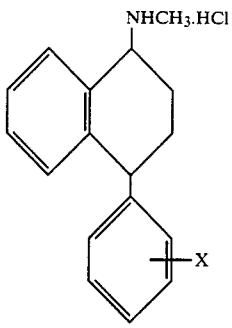

| Example Number | X | M.P. (°C.) | Molecular Formula | Elemental Analysis | | | | | |
|---|---|---|---|---|---|---|---|---|---|
| | | | | Calculated (%) | | | Found (%) | | |
| | | | | C | H | N | C | H | N |
| 18 | 2-OCH$_3$ | 247–248 | C$_{18}$H$_{21}$ON.HCl.½H$_2$O | 69.99 | 7.37 | 4.53 | 70.10 | 7.33 | 4.76 |
| 19 | 3-OCH$_3$ | 226–227 | C$_{18}$H$_{21}$ON.HCl.¼H$_2$O | 70.12 | 7.35 | 4.54 | 70.29 | 7.67 | 4.60 |

EXAMPLE 20

Cis-(1S)(1R)-N-methyl-4-(2,4-dichlorophenyl)-1,2,3,4-tetrahydro-1-naphthalenamine Hydrochloride In like manner to that described in Example 15, the named compound (cis-racemate, m.p. 288°–289° C.) was prepared from 2,4-dichlorobenzophenone.

EXAMPLE 21

Cis-(1S)(1R)-N-methyl-4-(4-chlorophenyl)-7-methoxy-1,2,3,4-tetrahydro-1-naphthalenamine Hydrochloride In like manner to that described in Example 17 A, D to F, the named compound (cis-racemate) was prepared from commercially available 4-bromochlorobenzene and 6-methoxy-1-tetralone. Steps B and C of Example 17 were omitted. The following procedure was employed in place of step 17G:

(G) Title Compound (Cis-Racemate)

A solution of N-methyl-4-(4-chlorophenyl)-7-methoxy-1,2-dihydro-1-naphthalenamine hydrochloride (1.6 g., 4.8 mmoles) in ethanol:tetrahydrofuran was treated with PtO$_2$ catalyst (1.0 g.), saturated with gaseous HCl and hydrogenated for two hours at room temperature and 50 psi of H$_2$. Isolated reaction product was converted to the free base and chromatographed on silica gel (elution with ethyl acetate containing 1% ammonium hydroxide) to separate the cis- and trans-isomers. The cis-isomer was converted to the hydrochloride salt, which was crystallized from ethyl acetate (300 mg., 19% yield, m.p. 276°–277° C., elemental analysis calculated: 63.91% C; 6.26% H; 4.14% N; found: 63.60% C; 6.40% H; 3.99% N).

EXAMPLE 22

Cis-(1S)(1R)-N,N-dimethyl-4-(3-trifluoromethylphenyl)-1,2,3,4-tetrahydro-1-naphthalenamine Maleate In like manner to that described in Example 7 A–D the named compound (cis-racemate) was prepared from 3-trifluoromethyl-benzophenone (m.p. 120°–121° C., ¼ mole H$_2$O per mole named compound, elemental analysis calculated: 62.79% C; 5.61% H; 3.18% N; found: 62.97% C; 5.49% H; 3.11% N). In place of step 7E, the following procedure was employed:

(E) Title Compound (Cis-Racemate)

A solution of 4-(3-trifluoromethylphenyl)-alphatetralone (3.0 g., 0.010 mole) in toluene (50 ml.) was treated, under cooling in an ice bath, with dimethylamine (3 ml., 0.045 mole) followed by titanium tetrachloride (dropwise addition, 1.2 ml., 0.011 mole). The reaction mixture was then stirred for 16 hours at room temperature, filtered and evaporated under vacuum to yield a crude 3,4-dihydro-1-dimethylamino-4-arylnaphthalene solid. The crude enamine was added to a mixture of glacial acetic acid (5 ml.), sodium borohydride (1.3 g., 0.034 mole) and tetrahydrofuran (50 ml.), and the resulting mixture stirred for 3 hours at room temperature. The reaction mixture was then evaporated under vacuum to an oily solid, which was treated with water (100 ml.) and extracted with ether (200 ml.). The ether extract was dried (MgSO$_4$), filtered and evaporated under vacuum to an oil. The oil was chromatographed on silica gel, using a 0.5% diethylamine/hexane solvent mixture for elution, to separate the cis- and trans-isomers. The cis-isomer was eluted first. The eluted fractions were evaporated under vacuum, dissolved several times in methanol and evaporated again under vacuum to an oil (0.99 g.). The oil was dissolved in methanol (15 ml.) and the methanol solution treated with maleic acid (0.36 g., 0.0031 mole), heated to dissolve the acid and then evaporated under vacuum to a semi-solid, which was crystallized by dissolution in ethyl acetate followed by addition of ether (0.80 g., 18% yield).

EXAMPLES 23–24

In like manner to that described in Example 22 the following compounds (cis-racemates) were prepared from the appropriate substituted benzophenones:

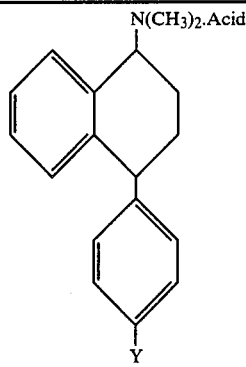

| Example Number | Y | M.P. (°C.) | Molecular Formula | Elemental Analysis Calculated (%) | | | Found (%) | | |
|---|---|---|---|---|---|---|---|---|---|
| | | | | C | H | N | C | H | N |
| 23 | $CF_3$ | 144–146 | $C_{19}H_{20}NF_3 \cdot C_4H_4O_4$ | 63.44 | 5.56 | 3.22 | 63.57 | 5.64 | 3.25 |
| 24 | Cl | 125–126 | $C_{18}H_{20}NCl \cdot \frac{3}{4}H_2O \cdot HCl$ | 64.39 | 6.75 | 4.17 | 64.25 | 6.82 | 4.02 |

EXAMPLE 25

Blockade of Synaptosomal Uptake of Serotonin (5HT), Dopamine (DA) and Norepinephrine (NE) In Vitro by Cis-(1S)-N-methyl-4-(3,4-dichlorophenyl)-1,2,3,4-tetrahydro-1-naphthalenamine Hydrochloride Sprague-Dawley CD male rats weighing 180–220 g. (Charles River Laboratories, Inc.; Wilmington, Mass.) were used in this procedure. A crude synaptosomal fraction of rat corpus striatum (for 5HT and DA uptake) or hypothalmus (for NE uptake) tissue was prepared by homogenizing tissue (25 ml./g. wet) in ice-cold 0.32M sucrose containing 1 mg./ml. glucose, 0.0001M EDTA and tris(hydroxymethyl)aminomethane to pH 7.4. The homogenate was centrifuged at 1000 × g for 10 min. at 0°–4° C., the pellet discarded and the supernatant centrifuged at 17,000 × g for 20 min. at 0°–4° C. The resulting pellet was resuspended in the ice-cold 0.32M sucrose pH 7.4 solution at 10 ml./g. original tissue (wet) for corpus striatum and 5 ml./g. original tissue (wet) for hypothalmus. An incubation buffer was prepared: 26mM tris(hydroxymethyl)aminomethane, adjusted to pH 7.4 with HCl, containing 124mM NaCl, 4.5mM KCl, 1.2mM $KH_2PO_4$, 1.3mM $MgCl_2 \cdot 6H_2O$, 0.001mM ascorbic acid, 0.0125mM nialamide hydrochloride and 2.8mM $CaCl_2$. Duplicate 0.1 ml. aliquots of the tissue suspension were incubated for 10 min. at 37° C. with 0.02 ml. of a solution containing a known quantity of the named test compound and 1.0 ml. of the incubation buffer containing additionally 1 mg./ml. glucose and 0.0001mM labeled monoamine ($^{14}C$-5HT, $^{14}C$-DA or $^3H$-NE). After incubation, the mixtures were filtered through 0.45 micron Millipore filters and the filters washed with the incubation buffer. The filtered materials were dissolved in 1.0 ml. of 2-methoxyethanol and analyzed for radioactivity by liquid scintillation counting (uptake at 0° C. taken as radiation blank). Uptake was calculated as picomoles 5HT, DA or NE per mg. protein (protein was determined by measurement with Folin phenol reagent). The $IC_{50}$, the concentration of named test compound (expressed as micromoles per liter in ca. 1 ml. incubation mixture) inhibiting uptake by 50% from that calculated for test compound-free control aliquots, was estimated from plots of % uptake inhibition vs. concentration on semilog paper to be 0.060 micromolar for 5HT, 1.3 micromolar for DA and 0.54 micromolar for NE. The ratio of $IC_{50}$(5HT) to $IC_{50}$(NE) was 0.11.

EXAMPLES 26–49

In like manner to that described in Example 25 the blockade of synaptosomal uptake was determined in vitro for the compounds listed below.

| Example Number | Compound Prepared in Example Number | $IC_{50}$ (micromoles/liter)[a] | | | $IC_{50}$ (5HT) / $IC_{50}$ (NE) |
|---|---|---|---|---|---|
| | | Corpus 5HT | Striatum DA | Hypothalmus NE | |
| 26 | 1 | 0.074 | 0.52 | 0.72 | 0.10 |
| 27 | 3 | 0.46 | 0.32 | 0.30 | 1.5 |
| 28 | 4 | 0.26 | 1.4 | 1.4 | 0.19 |
| 29 | 5 | 0.46 | 3.5 | 5.0 | 0.092 |
| 30 | 6 | 2.1 | 1.5 | 1.2 | 1.7 |
| 31 | 7 | 1.7 | 4.7 | 2.3 | 0.74 |
| 32 | 8 | 0.82 | 7.8 | 9.8 | 0.084 |
| 33 | 9 | 1.1 | 6.4 | 9.4 | 0.12 |
| 34 | 10 | 2.2 | 5.6 | 12 | 0.18 |
| 35 | 11 | 0.25 | 2.5 | 2.5 | 0.10 |
| 36 | 12 | 0.22 | 1.5 | 4.3 | 0.051 |
| 37 | 13 | 0.35 | 6.8 | 3.6 | 0.10 |
| 38 | 14 | 1.3 | 0.55 | 2.4 | 0.54 |
| 39 | 15 | 0.30 | 1.3 | 2.2 | 0.14 |
| 40 | 16 | 0.19 | 1.6 | 1.4 | 0.14 |
| 41 | 17 | 0.70 | 4.2 | 3.0 | 0.23 |
| 42 | 18 | 4.2 | 11 | 2.3 | 1.8 |
| 43 | 19 | 7.6 | 5.0 | 1.4 | 5.4 |
| 44 | 20 | 0.5 | 1.7 | 0.31 | 1.61 |
| 45 | 21 | 0.19 | 0.44 | 0.47 | 0.40 |
| 46 | 22 | 0.19 | 7.0 | 0.89 | 0.21 |
| 47 | 23 | 0.35 | 12 | 14 | 0.025 |
| 48 | 24 | 0.24 | 5.6 | 1.2 | 0.20 |
| 49 | Comparative[b] Example | 3.5 | 5.1 | 1.9 | 1.8 |

[a] H = high activity, M = moderate activity,
L = low activity. For 5HT and DA uptake blockade:
H, $IC_{50}$ less than 1 micromolar; M, $IC_{50}$ 1–5 micromolar;
L, $IC_{50}$ greater than 5 micromolar. For NE uptake blockade:
H, $IC_{50}$ less than 0.1 micromolar; M, $IC_{50}$ 0.1–0.5 micromolar; L, $IC_{50}$ greater than 0.5 micromolar.
[b] Cis-(1S) (1R)-N—methyl-4-phenyl-1,2,3,4-tetrahydro-1-naphthalenamine hydrochloride (U.S. Pat. No. 4,029,731).

EXAMPLE 50

Potentiation of 5-Hydroxytryptophan-induced Behavioral Symptoms In Vivo by Cis-(1S)-N-methyl-4-(3,4-dichlorophenyl)-1,2,3,4-tetrahydro-1-naphthalenamine Hydrochloride Groups of 10 fasted Swiss-Webster CD male mice weighing 17–21 g. (Charles River Laboratories, Inc.; Wilmington, Mass.) were given varying oral doses of the named test compound and 100 mg./kg. body weight intraperitoneal doses of 5-hydroxytryptophan (5HTP) one hour later. This dose of 5HTP causes by itself no clear behavioral effects, but it causes a syndrome including tremors in mice treated with serotonin uptake blockers. The mice were rated for the presence of this symptom by a "blinded observer" at 10–20 min. after 5HTP treatment. An $ED_{50}$ value (oral dosage level at which symptom elicited) was estimated to be 1.0 mg./kg. body weight for tremors.

EXAMPLES 51–67

In like manner to that described in Example 50 the potentiation of 5-hydroxytryptophan-induced tremors was determined in vivo for the compounds listed below.

| Example Number | Compound Prepared in Example Number | $ED_{50}$ (mg./kg. - oral) |
| --- | --- | --- |
| 51 | 1 | 3.2–5.6 |
| 52 | 3 | b |
| 53 | 4 | 10–32 |
| 54 | 5 | a |
| 55 | 6 | a |
| 56 | 7 | b |
| 57 | 8 | 10–32 |
| 58 | 9 | <32 |
| 59 | 10 | b |
| 60 | 11 | 10–32 |
| 61 | 12 | 1.0–3.2 |
| 62 | 13 | 3.2–10 |
| 63 | 14 | b |
| 64 | 18 | b |
| 65 | 22 | 3.2–10 |
| 66 | 23 | 32–56 |
| 67 | Comparative Example[c] | b |

[a] No observed tremors at 10 mg./kg., highest dose tested.
[b] No observed tremors at 32 mg./kg., highest dose tested.
[c] Cis-(1S) (1R)-N—methyl-4-phenyl-1,2,3,4-tetrahydro-1-naphthalenamine hydrochloride (U.S. Pat. No. 4,029,731).

EXAMPLE 68

Ability of Cis-(1S)-N-methyl-4-(3,4-dichlorophenyl)-1,2,3,4-tetrahydro-1-naphthalenamine Hydrochloride to Counteract Reserpine - induced Hypothermia in Mice In Vivo A number of Swiss-Webster CD male mice (17–21 g. Charles River) were placed in a room with an ambient temperature of 20° C. The mice were individually housed in plastic chambers with a cardboard bottom. All mice were injected with reserpine subcutaneously at 2 mg./kg. body weight and retained at 20° C. for 18 hours. The rectal temperatures of the mice were then measured and immediately thereafter the mice were divided into groups of five for testing. Each group received oral administration of either saline (controls) or the named test compound (10 mg./kg. body weight), and the resulting rectal temperatures measured two hours later. The mean rectal temperature (+S.D.) in the five mice treated with the named test compound was 20.3°±0.3° C. at the 2-hour mark, compared to a mean in the twenty mice in the control group of 20.4°±1.2° C. at the 2-hour mark. This finding is consistent with other indications in the art that counteraction of reserpine hypothermia correlates with inhibition of norepinephrine uptake, but not with inhibition of serotonin uptake.

EXAMPLE 69

Ability of Cis-(1S)-N-methyl-4-(3,4-dichlorophenyl)-1,2,3,4-tetrahydro-1-naphthalenamine Hydrochloride to Antagonize Para-chloroamphetamine(PCA) - induced Depletion of Serotonin from Rat Brain In Vivo Serotonin uptake blockers show a dose-dependent antagonism of the serotonin-depleting action of PCA, a drug which requires 5HT uptake into 5HT neurons to exert its effect. Sprague-Dawley CD male rats (180–220 g. Charles River) in groups of five received two simultaneous subcutaneous injections: either the named test compound (at different dosage levels) +6.6 mg./kg. body weight PCA, water+6.6 mg./kg. body weight PCA, or water+water (controls). The rats were decapitated four hours later and their whole brain assayed for serotonin content by the Bogdanski method. Homogenates of brain in 0.1N HCl were made alkaline with borate buffer and extracted with butanol. The solvent phase was then extracted with 0.1N HCl. The aqueous extracts were acidified with concentrated HCl and the intrinsic fluorescence of serotonin measured in a spectrophotofluorometer. The $ED_{50}$, i.e. the dose giving a 50% reversal of the PCA-induced serotonin depletion, was estimated graphically on semilog paper to be 0.2 mg./kg. body weight.

EXAMPLE 70

Reduction of Behavioral Despair In Vivo (Modified Porsolt Method) by Cis-(1S)-N-methyl-4-(3,4-dichlorophenyl)-1,2,3,4-tetrahydro-1-naphthalenamine Hydrochloride A modification of the procedure described by Porsolt et al., *Arch. Int. Pharmacodyn.*, 229, pp. 327–336 (1977) was used. A number of Swiss-Webster CD male mice weighing 25–30 g. (Charles River Laboratories, Inc.; Wilmington, Mass.) were housed under standard laboratory conditions for at least one week prior to experimentation. Groups of 10 mice were then injected subcutaneously with either a given dosage of the named test compound or vehicle (5% Emulphor: 5% ethanol: 90% normal saline). One hour later the mice were placed individually in 1 liter beakers containing 7 cm. of 25° C. water. Beginning at 2 min. after immersion, each mouse was observed every 30 sec. for the presence of immobility, characterized as floating motionless in the water. A total of ten observations were made, each being scored as "0=animal moving, swimming, attempting to escape" or "1=animal immobile". The number of positive observations for each mouse was then totaled and a mean immobility score calculated for the group of ten. For dose-response analysis, this data was converted to % MPE (maximum possible effect) values, defined as:

$$\% \text{ MPE} = \frac{\text{Control mean} - \text{Test mean}}{\text{Control mean}} \times 100\%$$

The following % MPE values were obtained for various dosages of the named test compound:

| Dosage (mg./kg.) | % MPE |
|---|---|
| 0.10 | 7.9 |
| 0.32 | 24 |
| 1.00 | 17 |
| 3.20 | 41 |
| 10.0 | 57 |
| 17.8 | 57 |
| 32.0 | 66 |

From the above data a % $MPE_{50}$ value, i.e. the dosage producing a 50% reduction in immobility relative to control, was determined by linear regression analysis to be 7.6 mg./kg. body weight for the named test compound.

EXAMPLES 71–77

In like manner to that described in Example 70 the reduction of behavioral despair in vivo was determined for the compounds listed below.

| Example Number | Compound Prepared in Example Number | $MPE_{50}$ (mg./kg.) |
|---|---|---|
| 71 | 1 | 4.5 |
| 72 | 3 | 19 |
| 73 | 7 | 138 |
| 74 | 11 | 42[a] |
| 75 | 18 | >32 |
| 76 | 22 | [b] |
| 77 | Comparative Example[c] | [d] |

[a] % MPE fell from 45 at 32.0 mg./kg. to 10 at 56.0 mg./kg., reflecting apparent overdosage. % MPE data above 32.0 mg./kg. dosage not included in calculation of $MPE_{50}$.
[b] No observed effect on immobility (relative to control) at 56.0 mg./kg. dosage.
[c] Cis-(1S) (1R)-N—methyl-4-phenyl-1,2,3,4-tetrahydro-1-naphthalenamine hydrochloride (U.S. Pat. No. 4,029,731).
[d] No observed effect on immobility (relative to control) at 32.0 mg./kg. dosage.

We claim:

1. A compound selected from the group consisting of cis-isomeric bases of the formula

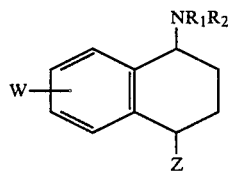

and the pharmaceutically acceptable acid addition salts thereof, wherein $R_1$ is selected from the group consisting of hydrogen and methyl, $R_2$ is methyl, Z is selected from the group consisting of 3-chlorophenyl, 4-chlorophenyl, 4-methoxyphenyl, 3-trifluoromethyl-phenyl, 4-trifluoromethyl-phenyl, 3,4-dichlorophenyl, 3-bromophenyl, 4-bromophenyl and 3-trifluoromethyl-4-chloro-phenyl, and W is selected from the group consisting of hydrogen, fluoro, chloro, bromo, trifluoromethyl and alkoxy of from 1 to 3 carbon atoms, with said compound being either the (1S)-enantiomer or the racemic mixture of the (1S)-enantiomer with the corresponding (1R)-enantiomer.

2. A compound of claim 1 wherein W is hydrogen.

3. A compound of claim 2 wherein Z is selected from the group consisting of 3,4-dichlorophenyl, 3-trifluoromethyl-phenyl, 4-chlorophenyl, 4-bromophenyl and 3-trifluoromethyl-4-chloro-phenyl.

4. A compound of claim 1 wherein W is 7-chloro.

5. A compound of claim 1 wherein $R_1$ is hydrogen.

6. A compound of claim 1 wherein $R_1$ is methyl.

7. A compound of claim 5 wherein W is hydrogen and Z is 3,4-dichlorophenyl.

8. A compound of claim 5 wherein W is hydrogen and Z is 4-bromophenyl.

9. A compound of claim 5 wherein W is hydrogen and Z is 4-chlorophenyl.

10. A compound of claim 5 wherein W is hydrogen and Z is 3-trifluoromethyl-phenyl.

11. A compound of claim 5 wherein W is hydrogen and Z is 3-trifluoromethyl-4-chloro-phenyl.

12. A compound of claim 6 wherein W is hydrogen and Z is 4-chlorophenyl.

13. A compound of claim 6 wherein W is hydrogen and Z is 3-trifluoromethyl-phenyl.

14. A compound of claim 6 wherein $R_1$ is hydrogen and Z is 4-chlorophenyl.

15. A compound of claim 1, 2, 3, 4, 5, 6, 8, 9, 10, 11, 12, 13 or 14 wherein said compound is the (1S)-enantiomer.

16. A compound of claim 1, 2, 3, 4, 5, 6, 8, 9, 10, 11, 12, 13 or 14 wherein said compound is the racemic mixture of the (1S)-enantiomer with the corresponding (1R)-enantiomer.

17. A compound of claim 7 wherein said compound is the (1S)-enantiomer.

18. A compound of claim 7 wherein said compound is the racemic mixture of the (1S)-enantiomer with the corresponding (1R)-enantiomer.

19. A method for combatting mental depression in a mentally-depressed subject which comprises administering to said subject an effective amount of a compound of claim 1.

20. A method for combatting mental depression in a mentally-depressed subject which comprises administering to said subject an effective amount of a compound of claim 7.

21. A pharmaceutical composition containing an amount effective in combatting mental depression of a compound of claim 1 as the essential active ingredient in a pharmaceutically acceptable carrier.

22. A pharmaceutical composition containing an amount effective in combatting mental depression of a compound of claim 7 as the essential active ingredient in a pharmaceutically acceptable carrier.

* * * * *

UNITED STATES PATENT AND TRADEMARK OFFICE

CERTIFICATE EXTENDING PATENT TERM
UNDER 35 U.S.C. § 156

PATENT NO.: 4,536,518

DATED: August 20, 1985

INVENTORS: Willard M. Welch, Jr. et al.

PATENT OWNER: Pfizer, Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,228 DAYS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks